US 6,659,984 B2

(12) United States Patent
Maclean Crawford et al.

(10) Patent No.: US 6,659,984 B2
(45) Date of Patent: Dec. 9, 2003

(54) NEEDLE ASSEMBLY

(75) Inventors: Jamieson William Maclean Crawford, New York, NY (US); Stefanie Livanos, Bethlehem, PA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 212 days.

(21) Appl. No.: 10/066,916

(22) Filed: Nov. 13, 2001

(65) Prior Publication Data
US 2002/0099340 A1 Jul. 25, 2002

Related U.S. Application Data
(60) Provisional application No. 60/259,875, filed on Jan. 5, 2001.

(51) Int. Cl.[7] .................................................. A61M 5/00
(52) U.S. Cl. ....................................... 604/263; 604/110
(58) Field of Search ........................... 604/110, 164.08, 604/165.03, 192, 197, 198, 263, 177, 162; 600/576, 577, 579

(56) References Cited

U.S. PATENT DOCUMENTS

| 5,219,339 | A | * | 6/1993 | Saito ............................ 604/198 |
| 5,330,438 | A | | 7/1994 | Gollobin et al. ............. 604/177 |
| 5,498,241 | A | | 3/1996 | Fabozzi ....................... 604/177 |
| 5,501,672 | A | | 3/1996 | Firth et al. .................. 604/177 |
| 5,779,679 | A | * | 7/1998 | Shaw .......................... 604/158 |

FOREIGN PATENT DOCUMENTS

| EP | 0475857 A1 | 3/1992 |
| WO | WO98/42393 | 10/1998 |
| WO | WO98/48883 | 11/1998 |
| WO | WO00/25845 | 5/2000 |
| WO | WO00/37125 | 6/2000 |

* cited by examiner

Primary Examiner—Michael J. Hayes
(74) Attorney, Agent, or Firm—Nanette S. Thomas, Esq.; Scott J. Rittman, Esq.

(57) ABSTRACT

An automatically shieldable blood collection set is provided. The blood collection set includes a needle assembly having a hub to which a needle cannula is fixedly attached. A safety shield is telescoped relative to the hub and the needle cannula and can be moved from a first position where the needle cannula is exposed to a second position where the needle cannula is safely shielded. A spring is provided between the shield and the hub to propel at least one of the shield and the hub into the second position. A retainer is provided for releasably holding the shield and the hub in the first position. A resiliently deflectable dorsal fin projects from the hub and through a slot in the shield. The dorsal fin can be deflected to release the retainer and permit the spring to drive the shield end up to the second position. The slot in the shield is configured to lockingly engage the dorsal fin when the shield and the hub are in the second position.

8 Claims, 2 Drawing Sheets

NEEDLE ASSEMBLY

This application claims the benefit of Provisional application No. 60/259,875 filed Jan. 5, 2001.

BACKGROUND OF THE INVENTION

1. Field of the Invention

The subject invention relates to a blood collection set having a needle cannula and a shield that can be driven in opposite directions to safely shield the needle cannula.

2. Description of the Related Art

A prior art blood collection set includes a small diameter needle cannula having a pointed distal end and a proximal end mounted to a thermoplastic hub. Portions of the blood collection set near the hub may be provided with a pair of flexible wings. The wings can be folded into face-to-face engagement with one another to facilitate digital manipulation of the small needle cannula. The wings then can be folded away from one another and taped into face-to-face engagement with the skin of the patient near a puncture site. The prior art blood collection set further includes a flexible plastic tube that has one end connected to the hub and an opposed end connected to a fitting. The fitting can be placed in communication with a reservoir to which collected blood may be directed.

The needle cannula of the prior art blood collection set typically is shielded prior to and after use to prevent accidental sticks. Needle shields used with prior art blood collection sets have taken many forms. Typically, a prior art blood collection set is packaged with a rigid tubular cap telescoped over the needle cannula to prevent accidental sticks prior to use. This tubular cap is removed from the needle cannula immediately prior to use of the blood collection set. Most prior art blood collection sets further include a second shield that is telescoped over the needle cannula and hub. The second shield may include at least one slot through which wings of the prior art hub may extend. Thus, the medical technician who uses the prior art blood collection set will hold the wings of the needle hub in one hand and the shield in the other hand after removing the needle cannula from the patient or blood donor. The wings then are slid proximally relative to the shield, thereby drawing the needle cannula into the shield. Some prior art shields are configured to engage the wings when the needle cannula has been shielded to make a re-exposure of the needle cannula difficult.

The digital manipulation that is required to shield the used needle cannula of a prior art blood collection set creates the potential for generating the accidental needle stick that the shield is intended to avoid. In particular, it is undesirable to rely upon a shielding that requires two hands to be moved in opposite directions in proximity to the point of a used needle cannula. Accordingly, the inventors herein have recognized the desirability of providing an automatically shieldable needle cannula for a blood collection set.

SUMMARY OF THE INVENTION

The subject invention relates to a blood collection set which comprises a needle cannula having a proximal end, a pointed distal end and a lumen extending therebetween. The blood collection set further includes a hub that may be molded from a thermoplastic material. The hub includes a proximal end, a distal end and a passage extending continuously therebetween. The distal end of the hub is securely mounted to the proximal end of the needle cannula. Thus the lumen through the needle cannula communicates with the passage through the hub. The hub further includes an outwardly extending actuator disposed at a location near the distal end of the hub. The hub further includes a dorsal fin that extends outwardly at a location spaced slightly proximally from the actuator. The dorsal fin and the actuator are disposed in a common radially aligned plane of the hub. Additionally, the dorsal fin can be deflected about its connection to the hub for engaging the actuator.

The blood collection set may further include a length of flexible tubing having opposed proximal and distal ends. The distal end of the flexible tubing may be connected to the proximal end of the hub such that the lumen through the needle cannula and the passage through the hub both communicate with the passage through the flexible tubing. The flexible tubing further includes a proximal end that may be connected to a fitting. The fitting may comprise a needle cannula that enables the blood collection set to be placed in communication with a reservoir for receiving a sample of blood. The tubing and the fitting may be of conventional design.

The blood collection set may further include a substantially rigid generally tubular safety cap mounted over the needle cannula for protection against accidental needle sticks prior to use of the blood collection set. The safety cap may include a proximal end that is frictionally engaged with the hub. The rigid tubular safety cap may be removed immediately prior to use of the blood collection set.

The blood collection set further includes a safety shield that is movable axially relative to the hub and cannula from a position, where the needle cannula is exposed, to a position, where the needle cannula is safely shielded. Biasing means are provided between the shield and the hub for urging the shield and the hub in opposite directions for shielding the needle. The biasing means may be a coil spring that surrounds a portion of the hub. A shield includes a slot extending longitudinally from a location near the proximal end to a location spaced slightly proximally from the distal end. The slot is dimensioned to slidably receive portions of the dorsal fin adjacent the hub. Portions of the slot near the proximal end of the shield define a restriction for gripping the dorsal fin and holding the dorsal fin at the proximal end of the slot. The safety shield also includes a retention opening between the slot and the extreme distal end of the safety shield. The retention opening is dimensioned to releasably engage the actuating projection formed on the hub.

The blood collection set initially has the needle cannula projecting distally beyond the shield. However, the safety cap is securely mounted over the needle cannula to prevent accidental sticks prior to use of the blood collection set. The safety cap then can be removed to permit use of the blood collection set substantially in a conventional manner. After use, the dorsal fin can be deflected distally and into engagement with the actuator. Contact between the dorsal fin and the actuator will urge the actuator out of the retention opening in the safety shield. Thus, the biasing means will drive the hub and the safety shield in opposite direction such that the safety shield surrounds the needle cannula. In some embodiments, the user may grip the dorsal fin such that the safety shield is driven forwardly or distally into surrounding relationship around the needle cannula. In other embodiments, the safety shield may include a pair of wings extending transversely from the safety shield. The wings may be gripped by a health care worker or taped to the patient. In this situation, the hub and the needle cannula will be driven rearwardly or proximally relative to the shield for retracting the needle cannula into the shield.

DETAILED DESCRIPTION

Figure 1:
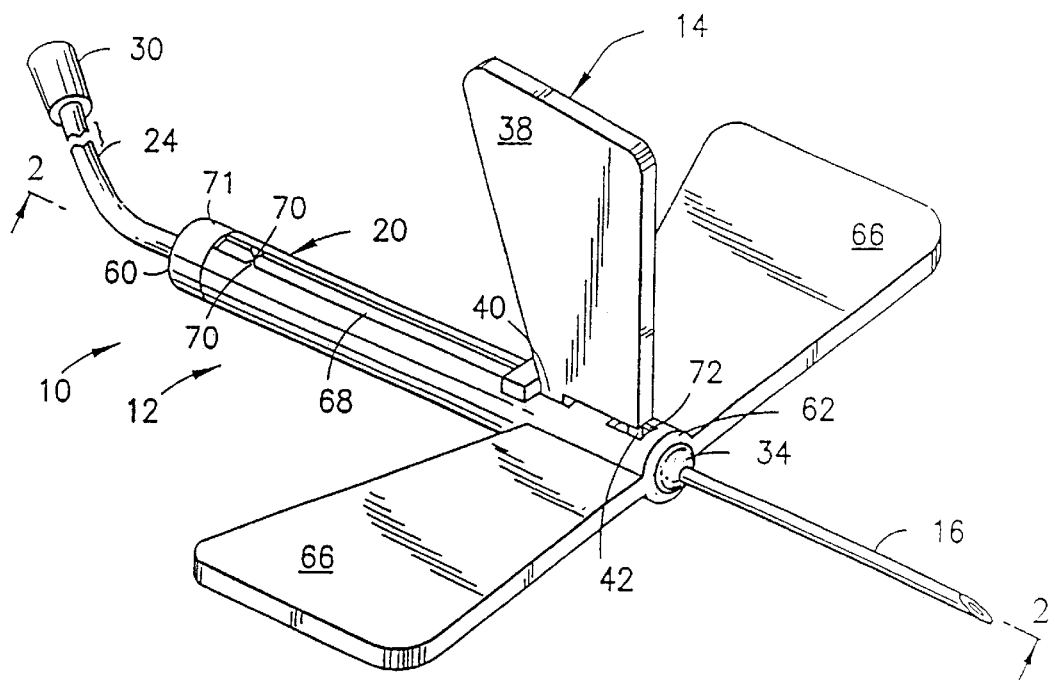
FIG. 1 is a perspective view of a blood collection set in accordance with the subject invention.
Figure 2:
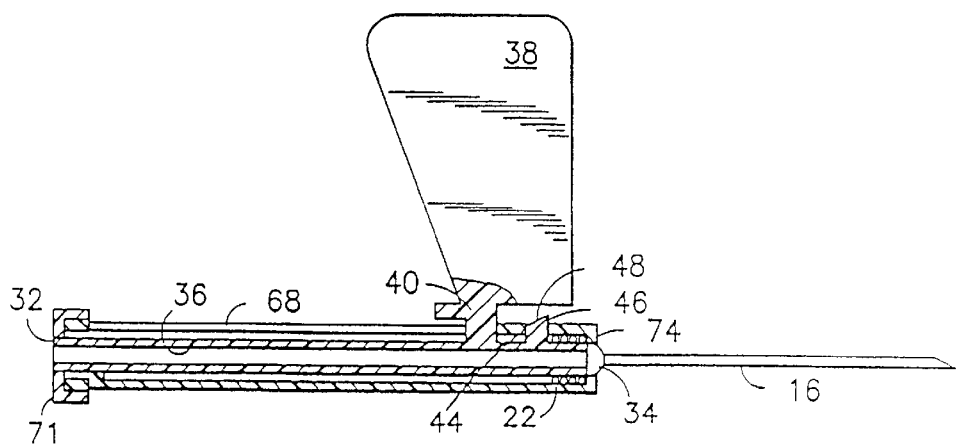
FIG. 2 is a cross-sectional view taken along line 2—2 in FIG. 1.
Figure 3:
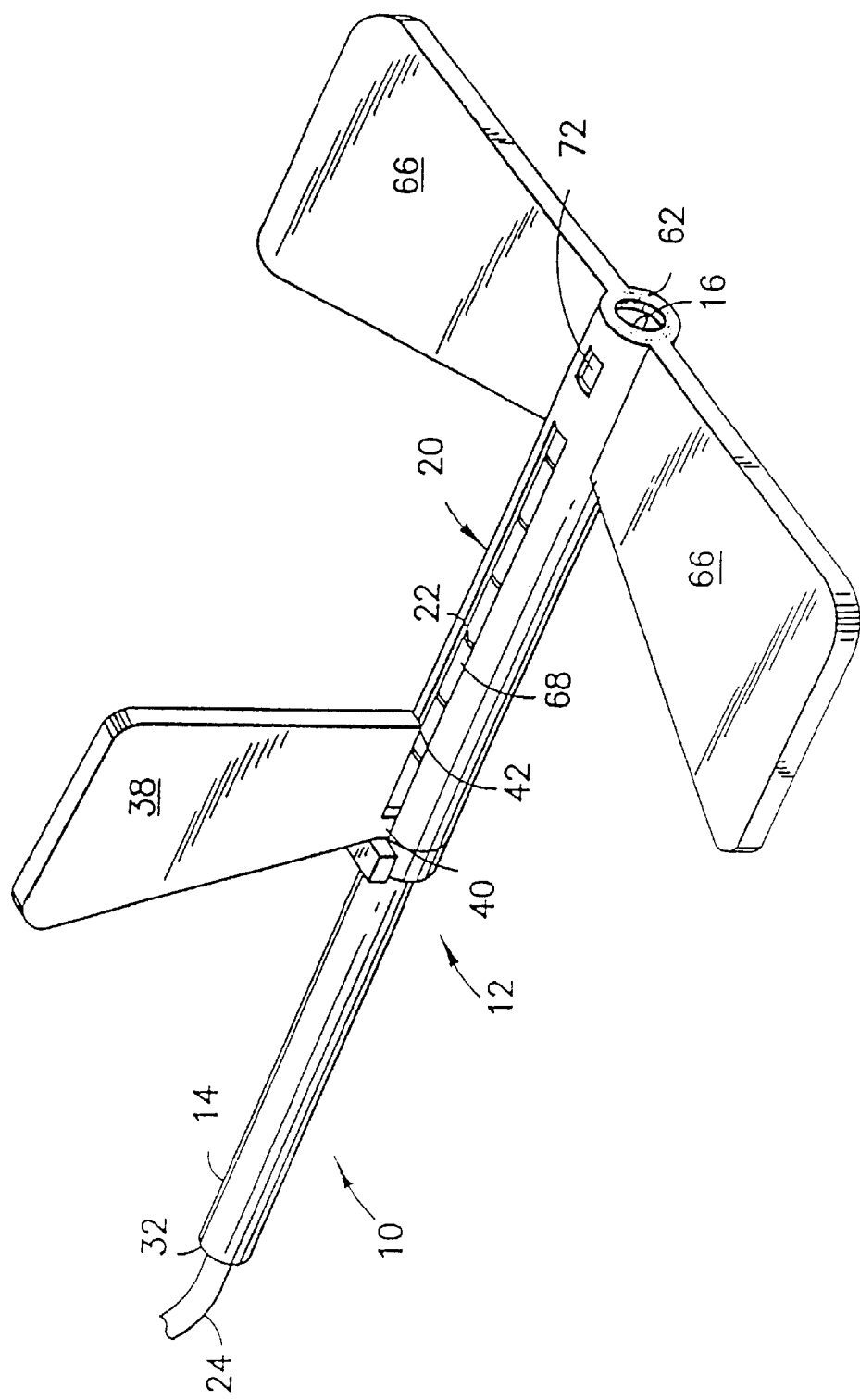
FIG. 3 is a perspective view similar to FIG. 1, but showing the needle in a fully shielded position.

A blood collection set in accordance with the subject invention is illustrated in FIGS. 1–3, and is identified generally by the numeral 10. Blood collection set 10 includes a needle assembly 12 which comprises a hub 14, a needle cannula 16, a safety shield 20 and a spring 22. Needle assembly 12 is used with a flexible tube 24 and a fitting 30. Fitting 30 can be connected to a reservoir into which blood drawn from needle assembly 12 may be deposited.

Hub 14 includes a proximal end 32 connected to flexible tubing 24, a distal end 34 connected to needle cannula 16 and a tubular passage 36 extending therebetween, as shown in FIG. 2. Hub 14 further includes a dorsal fin 38 projecting unitarily outwardly from a portion of hub 14 intermediate proximal and distal ends 32 and 34. Dorsal fin 38 is connected to remaining portions of hub 14 by a narrow deflectable root 40. An actuator 42 projects outwardly from hub 14 at a location between root 40 of dorsal fin 38 and distal end 34 of hub 14. Actuator 42 is substantially registered with distal portions of dorsal fin 38. As a result, dorsal fin 38 can be deflected about root 40 and into contact with actuator 42.

Actuator 42 has a proximal face 44 and a distal face 46 that is radially longer than proximal face 44. A ramp face 48 extends between proximal and distal faces 44 and 46.

Shield 20 is an elongate tubular member having a proximal end 60 and a distal end 62. The inside diameter of shield 20 is greater than the sum of the hub 14 plus the radial length of distal face 46 of actuator 42. Shield 20 includes a pair of flexible wings 66 extending transversely therefrom. Additionally, shield 20 includes an elongate slot 68 extending from proximal end 60 toward distal end 62 at a location that is angularly between fins 66. Slot 68 is dimensioned to slidably receive root 40 of dorsal fin 38. A pair of detents 70 are formed in slot 68 and extend toward one another at a location near the proximal end of shield 14. An annular closure 71 is mounted over proximal end 60 of shield 20 and closes the proximal end of slot 68.

A retention aperture 72 extends through shield 20 at a location aligned with slot 68 and slightly distally therefrom. The spacing between slot 68 and retention aperture 72 substantially equals the distance between root 40 and actuator 42. Additionally, retention aperture 72 is dimensioned to receive actuator 42 when dorsal fin 48 and root 40 are in a distal position in slot 42. Distal end 62 of shield 20 is formed with an inwardly extending flange 74. Spring 22 is positioned in shield 20 between inwardly extending flange 74 and actuator 42.

Needle assembly 12 is assembled by initially sliding spring 22 into proximal end 60 of shield 20. Hub 14 then is slid into proximal end 60 of shield 20 such that root 40 of dorsal fin 38 is slidably received in slot 68. Annular closure 71 then is securely mounted over proximal end 60 of shield 20, such that proximal end 32 of hub 14 passes through the central aperture of annular closure 71. Hub 14 is slid distally in shield 20 until actuator 42 aligns with retention aperture 72 in shield 20. Engagement between actuator 42 and portions of shield 20 adjacent retention aperture 72 will releasably retain shield 20 in the proximal position shown in FIGS. 1 and 2 relative to hub 14. Needle cannula 16 will be covered by a safety cap (not shown) until immediately prior to use of blood collection set 10.

Blood collection set 10 is used by removing the safety cap and inserting needle cannula 16 into a patient in a conventional manner. Digital manipulation of needle assembly 12 can be facilitated by deflecting wings 66 toward one another to define a grip. After collection of a sufficient volume of blood, needle cannula 16 is removed from the patient. Shielding is achieved merely by deflecting dorsal fin 38 in a distal direction and around root 40. Dorsal fin 38 will deflect into actuator 42 and will move actuator 42 transversely in shield 20 a sufficient distance for proximal face 44 to move inside the passage of shield 20. Spring 22 will then force ramp face 48 to ride over portions of shield 20 adjacent retention aperture 72 and will continue propelling hub 14 and shield 20 in opposite directions relative to one another. Root 40 then will advance proximally of detents 70, and will be lockingly retained at the extreme proximal end of slot 68 as shown in FIG. 3. Re-exposure of needle cannula 16 can be achieved only by significantly deforming and damaging shield 20, and cannot be achieved by mere inadvertence. As described above, deflection and then retention of dorsal fin 38 will cause shield 20 to be propelled distally. However, a user of the blood collection set 10 can hold onto wings 66 without holding onto dorsal fin 38. With this gripping, blood collection set 10 becomes a needle retracting device with hub 14 and needle cannula 16 being propelled in a proximal direction by spring 22.

What is claimed is:

1. A needle assembly for a blood collection set comprising:
   a hub having opposite proximal and distal ends and a passage extending between the ends, a resiliently deflectable dorsal fin projecting outwardly from said hub;
   a needle cannula having a proximal end connected to said distal end of said hub, a distal end and a lumen extending therebetween, said lumen providing fluid communication with said passage through said hub;
   a shield telescoped over said hub and said needle cannula such that at least one of said shield and said hub are movable from a first position where said needle cannula is exposed to a second position where said needle cannula is shielded, a slit extending through said shield and slidably receiving a portion of said dorsal fin, one end of said slit being configured for lockingly engaging said dorsal fin when said shield and said hub are in said second position;
   a spring captured between portions of said hub and said shield and operative for propelling said shield and said hub into said second position; and
   a retainer for releasably retaining said shield in said first position, said retainer being engageable by said deflectable dorsal fin for releasing said hub and said shield from said first position and enabling said spring to propel at least one of said shield and said hub to said second position.

2. The needle assembly of claim 1, wherein the resiliently deflectable dorsal fin includes a narrow root for joining said dorsal fin to said hub, said dorsal fin being deflectable in proximal and distal directions relative to said root.

3. The needle assembly of claim 2, wherein said root defines said portion of said dorsal fin that is engaged in said slot.

4. The needle assembly of claim 1, wherein said shield includes opposed proximal and distal ends, said slit extending from a location in proximity to said proximal end to a location located proximally of said distal end, portions of said slit spaced distally from said proximal end comprising a pair of detents for narrowing said slit, movement of said shield and said hub to said second position enabling said detents to lockingly trap said dorsal fin between said detents and said proximal end of said shield.

5. The needle assembly of claim 4, wherein said shield further comprises a retention aperture formed therethrough at a location between said slit and said distal end of said shield, said retainer comprising a projection extending from said hub and extending into said retention aperture of said shield when said shield and said hub are in said first position.

6. The needle assembly of claim 5, wherein the retention aperture is aligned with said slit and wherein said resiliently deflectable dorsal fin is configured for engaging said retainer and urging said retainer out of said retention aperture and thereby enabling said spring to propel at least one of said shield and said hub into said second position.

7. The needle assembly of claim 1, wherein said shield further comprises a pair of wings projecting transversely from said shield.

8. The needle assembly of claim 7, wherein the wings are disposed to lie substantially on opposite respective sides of said dorsal fin when said shield and said hub are in said first position.

* * * * *